United States Patent [19]
Kondoh et al.

[11] Patent Number: 5,917,073
[45] Date of Patent: Jun. 29, 1999

[54] ORGANIC ALUMINOXY COMPOUND AND CATALYST FOR PRODUCING POLYMER

[75] Inventors: Tsuyoshi Kondoh; Shoji Naganuma; Norio Tomotsu, all of Ichihara, Japan

[73] Assignee: Idemitsu Petrochemical Co., Ltd., Tokyo, Japan

[21] Appl. No.: 08/875,606

[22] PCT Filed: Dec. 19, 1996

[86] PCT No.: PCT/JP96/03699

§ 371 Date: Aug. 5, 1997

§ 102(e) Date: Aug. 5, 1997

[87] PCT Pub. No.: WO97/23488

PCT Pub. Date: Jul. 3, 1997

[30] Foreign Application Priority Data

Dec. 21, 1995 [JP] Japan ................................ 7-333338

[51] Int. Cl.⁶ .............. C07F 5/06; C07F 17/00; B01J 31/00
[52] U.S. Cl. .............. 556/175; 556/179; 556/182; 502/103; 502/117; 526/160; 526/943
[58] Field of Search ................ 556/175, 179, 556/182; 502/103, 117; 526/160, 943

[56] References Cited

FOREIGN PATENT DOCUMENTS 4-266891  9/1992  Japan .

OTHER PUBLICATIONS

Chemical Abstracts, vol. 123, abstract No. 314830, 1995.

*Primary Examiner*—Porfirio Nazario-Gonzalez
*Attorney, Agent, or Firm*—Oblon, Spivak, McClelland, Maier & Neustadt, P.C.

[57] ABSTRACT

An organic aluminoxy compound which shows $^{27}$Al nuclear magnetic resonance spectrum ($^{27}$Al-NMR spectrum) having an $A_1/A_2$ ratio of at most 0.1, wherein $A_1$ is area of a region encompassed by a segment of a line which connects a local minimum point existing between a continuous curve "a" containing a peak appearing at around 150 ppm and a continuous curve "b" containing a peak appearing at around 60 ppm to the point where the above curve "b" comes into contact with the base line and also by the above curve "b" and $A_2$ is area of a region encompassed by the above curves "a" and "b" and also by the base line; an organic aluminoxy compound containing at least 5%, expressed in terms of aluminum atom, of a portion insoluble in a mixed solvent of toluene and hexane in a ratio by volume of 2:5 at 30° C. or lower; and a catalyst for producing a polymer comprising any of the above organic aluminoxy compounds and a transition metal compound.

The above catalyst is a homogeneous catalyst having high and stable activity and used for polymerization of olefins and styrenes.

15 Claims, 1 Drawing Sheet

FIG. 1

ORGANIC ALUMINOXY COMPOUND AND CATALYST FOR PRODUCING POLYMER

CROSS-REFERENCES TO RELATED APPLICATIONS

This application was filed as a request for U.S. examination under 35 U.S.C. §371 of International application No. PCT/JP96/03699 filed Dec. 19, 1996.

TECHNICAL FIELD

The present invention relates to an organic aluminoxy compound and a catalyst for producing a polymer comprising the organic aluminoxy compound. More particularly, the present invention relates to an organic aluminoxy compound which provides a homogeneous catalyst having high and stable catalyst activity and a homogeneous catalyst for producing a polymer which comprises the above organic aluminoxy compound as a component and has high and stable catalyst activity.

BACKGROUND ART

As the process for polymerizing polymerizable unsaturated compounds, such as olefins and styrenes, to produce homopolymers and copolymers, processes using catalysts which comprise a transition metal compound, an ionic compound or an organic aluminoxy compound which can form an ionic complex compound by reaction with the transition metal compound, and optionally, a metal compound containing alkyl group have heretofore been known.

In the above homogeneous polymerization catalysts, the organic aluminoxy compound used as a component is a reaction product of an organoaluminum compound and water and forms a coordination polymerization catalyst by reaction with the transition metal compound. However, the known polymerization catalysts prepared by using an organic aluminoxy compound have a drawback in that polymers cannot be produced with stability and high activity because the properties of the catalyst show large dispersion.

DISCLOSURE OF THE INVENTION

Under the above circumstances, the present invention has an object of providing an organic aluminoxy compound which provides a homogeneous polymerization catalyst having high and stable catalyst activity. The present invention has another object of providing a catalyst for producing a polymer which comprises the above organic aluminoxy compound as a component and has high and stable activity.

As the result of the extensive studies undertaken by the present inventors to achieve the above objects, it was discovered that organic aluminoxy compounds having specific characteristics provides a homogeneous catalyst having high and stable catalyst activity and that a catalyst for producing a polymer which comprises a combination of the organic aluminoxy compound, a transition metal compound, and optionally, a metal compound containing alkyl group has stable and high activity. The present invention has been completed on the basis of the discoveries.

Accordingly, the present invention provides:
(1) An organic aluminoxy compound (I) which shows $^{27}$Al nuclear magnetic resonance spectrum (hereinafter referred to as $^{27}$Al-NMR spectrum) having an $A_1/A_2$ ratio of at most 0.1, wherein $A_1$ is area of a region encompassed by a segment of a line which connects a local minimum point existing between a continuous curve "a" containing a peak appearing at around 150 ppm and a continuous curve "b" containing a peak appearing at around 60 ppm to the point where the above curve "b" comes into contact with the base line and also by the above curve "b" and $A_2$ is area of a region encompassed by the above curves "a" and "b" and also by the base line;
(2) An organic aluminoxy compound (II) containing at least 5%, expressed in terms of aluminum atom, of a portion insoluble in a mixed solvent of toluene and hexane in a ratio by volume of 2:5 at 30° C. or lower;
(3) A catalyst for producing a polymer comprising (A) a transition metal compound and (B) organic aluminoxy compound (I) and/or (II); and
(4) A catalyst for producing a polymer comprising (A) a transition metal compound, (B) organic aluminoxy compound (I) and/or (II), and (C) a metal compound containing alkyl group.

THE MOST PREFERRED EMBODIMENT TO CARRY OUT THE INVENTION

Organic aluminoxy compound (I) of the present invention shows $^{27}$Al-NMR spectrum having the following characteristic.

The apparatus for the measurement is not limited to the apparatus stated in the Description.

Figure 1:
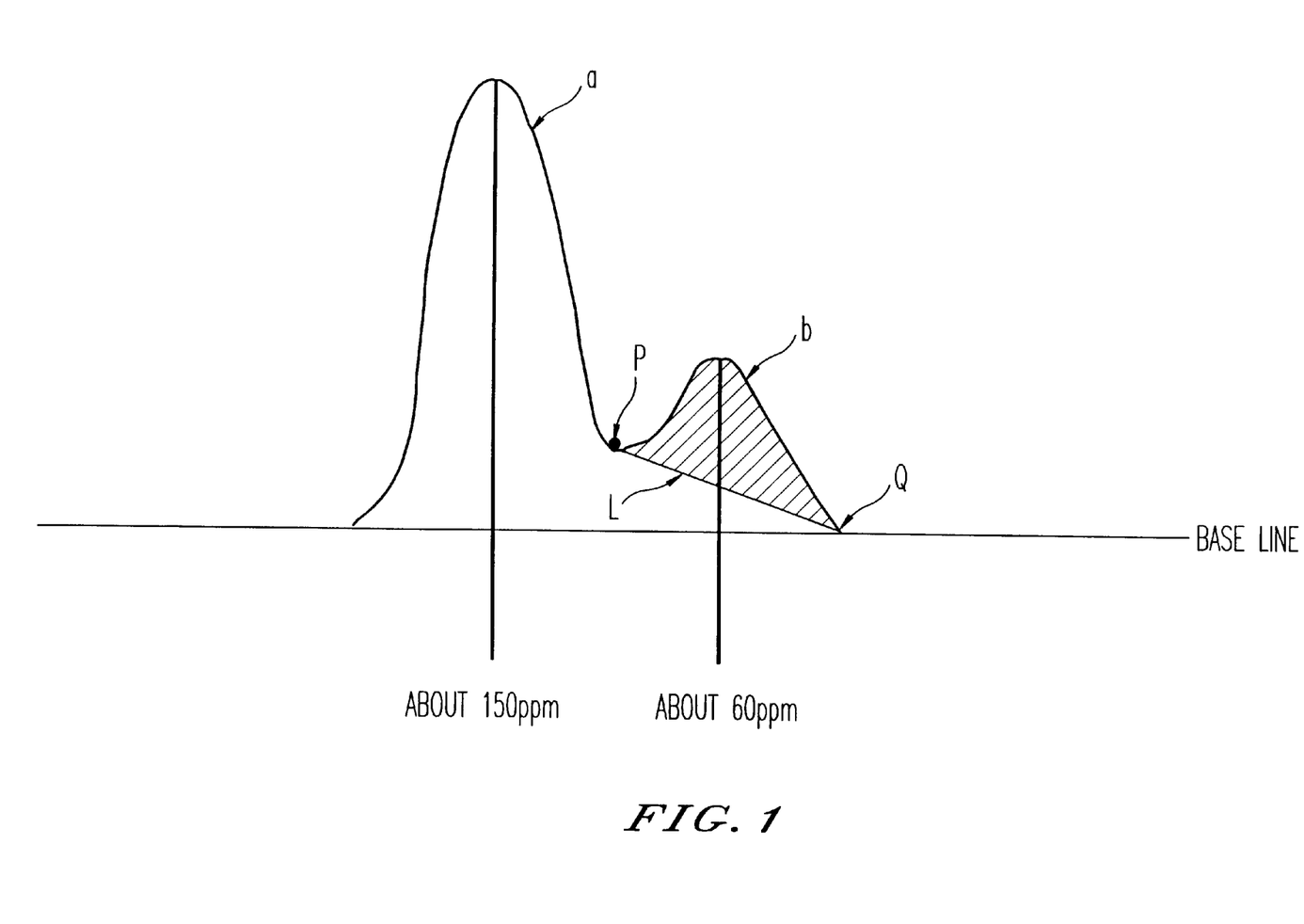
FIG. 1 is a schematic representation showing $^{27}$Al-NMR spectrum of an organic aluminoxy compound for describing the $A_1/A_2$ ratio in $^{27}$Al-NMR spectrum of the organic aluminoxy compound of the present invention.

FIG. 1 is a schematic representation showing $^{27}$Al-NMR spectrum of an organic aluminoxy compound. The curve containing a peak appearing at around 150 ppm is designated as "a", and the curve containing a peak appearing at around 60 ppm is designated as "b". The curves "a" and "b" form a continuous line. The area of a region encompassed by a segment of a line L which connects a local minimum point P existing between the continuous curve "a" and the continuous curve "b" to the point Q where the above curve "b" comes into contact with the base line and also by the above curve "b" is designated as $A_1$. The area of a region encompassed by the above curves "a" and "b" and also by the base line is designated as $A_2$. $^{27}$Al-NMR spectrum of the organic aluminoxy compound of the present invention has a ratio of $A_1$ to $A_2$ (an $A_1/A_2$ ratio) of at most 0.1.

The peaks on the $^{27}$Al-NMR spectrum are each shifted depending upon the measuring instruments to be used as well as the state of aluminoxy compound as a sample such as its purity, molecular weight, molecular structure, compounding ratio of chain aluminoxy compounds to cyclic aluminoxy compound and the state of its association. With regard to the aluminoxy compound as well, the peak on the curve "a" usually appears at around 150 ppm, but sometimes appears between 140 and 160 ppm or as the case may be, between 130 and 170 ppm.

Likewise, the peak on the curve "b" usually appears at around 60 ppm, but sometimes appears between 40 and 80 ppm or as the case may be, between 40 and 100 ppm.

When the $A_1/A_2$ ratio is at most 0.1, the catalyst for producing a polymer comprising the organic aluminoxy compound as a component has high activity, and moreover the activity is stable. In contrast, when $^{27}$Al-NMR spectrum of an organic aluminoxy compound has an $A_1/A_2$ ratio of more than 0.1, the catalyst for producing a polymer comprising this organic aluminoxy compound as a component shows large dispersion in the activity, and producing a polymer with stability and high activity becomes difficult.

$^{27}$Al-NMR spectrum described above is measured under the following condition by using a sample which is prepared by placing a solution prepared by dissolving 25 mg, expressed in terms of aluminum atom, of an organic aluminoxy compound in 0.6 ml of toluene into an NMR tube having a diameter of 5 mm and made of quartz.

Apparatus for the measurement:
  a product of NIPPON DENSHI Co., Ltd.; JNM-Gx270
Frequency of the measurement:
  70.282 MHz
Range of the measurement:
  151515 Hz
External reference:
  an aqueous solution of aluminum sulfate (0 ppm)
Time interval of repeated measurements:
  0.6 sec
Number of repeated measurements:
  10,000

Organic aluminoxy compound (II) having the following characteristic also exhibits the properties as excellent as those of organic aluminoxy compound (I) described above.

Organic aluminoxy compound (II) contains at least 5%, expressed in terms of aluminum atom, of a portion insoluble in a mixed solvent of toluene and hexane in a ratio by volume of 2:5 at 30° C. or lower. When the content of the insoluble portion is at least 5%, the catalyst comprising the organic aluminoxy compound as a component has a high activity, and moreover the activity is stable. In contrast, when an organic aluminoxy compound contains less than 5%, expressed in terms of aluminum atom, of the insoluble portion, the catalyst for producing a polymer comprising the organic aluminoxy compound as a component shows large dispersion in the activity, and producing a polymer with stability and high activity becomes difficult.

The content of the insoluble portion described above is obtained by the following method.

An organic aluminoxy compound in an amount of about 800 mg, expressed in terms of aluminum atom, is dissolved in 20 ml of toluene. To the obtained solution, 50 ml of hexane is added, and the resultant solution is filtered at 25° C. by using a glass filter prepared by WHATMAN Corporation. The amounts (mmol) of aluminum atom contained in the insoluble portion and in the soluble portion are measured, and the content of the insoluble portion is obtained from the thus obtained values.

The process for producing organic aluminoxy compounds (I) and (II) of the present invention is not particularly limited as long as organic aluminoxy compounds having the above characteristics can be obtained. When organic aluminoxy compounds are produced in accordance with the following process, organic aluminoxy compounds (I) and (II) can be obtained efficiently without large dispersion in the characteristics.

The organic aluminoxy compound is obtained by the reaction of an organoaluminum compound and water. As water used for the reaction, water of crystallization generally contained in a compound such as a metal salt, absorbed water contained in an inorganic compound or an organic compound, or water itself is used. It is advantageous that water of crystallization contained in a metal salt or a water itself is used as water for the reaction.

Therefore, the processes for producing the organic aluminoxy compound of the present invention can be classified into the process comprising the reaction of an organoaluminum compound and a metal salt containing water of crystallization and the process comprising the reaction of an organoaluminum compound and water itself.

When the organic aluminoxy compound is prepared by the process comprising the reaction of an organoaluminum compound and a metal salt containing water of crystallization, it is important that both components are brought into the reaction in such amounts that the ratio by mol of water taking part in the reaction to the organoaluminum compound is in the range of 0.5 to 1.0. When the ratio by mol is less than 0.5, the content of the portion insoluble in the mixed solvent of toluene and hexane is insufficient. When the ratio by mol is more than 1.0, obtaining the organic aluminoxy compound having the desired characteristics with stability tends to be difficult. The amount of the water taking part in the reaction means the amount of water of crystallization which can take part in the reaction.

In the reaction of an organoaluminum compound and a metal salt containing water of crystallization, the method of bringing both components into contact with each other is not particularly limited. For example, a metal salt containing water of crystallization is dispersed in a suitable organic solvent, and an organoaluminum compound is added to the dispersion. As other examples, a metal salt containing water of crystallization is added to a solution prepared by dissolving an organoaluminum compound in an organic solvent, or an organoaluminum compound and a metal salt containing water of crystallization are simultaneously added to an organic solvent. Because the reaction of water of crystallization in a metal salt and an organoaluminum compound proceeds slowly, the whole amounts of the components may be brought together at once without taking a long time.

The temperature of the reaction is not particularly limited. The temperature is generally selected in the range of −100 to 50° C., preferably in the range of −78 to 30° C., more preferably in the range of −10 to 30° C. The time of the reaction is varied depending on the temperature and cannot generally be decided. The time is usually in the range of about 0.1 to 10 hours, preferably in the range of 0.5 to 7 hours.

When the organic aluminoxy compound is prepared by the reaction of an organoaluminum compound and water itself, it is important that both components are brought into the reaction in such amounts that the ratio by mol of used water to the organoaluminum compound is in the range of 0.5 to 1.0. When the ratio by mol is less than 0.5, the content of the portion insoluble in the mixed solvent of toluene and hexane is insufficient. When the ratio by mol is more than 1.0, obtaining the organic aluminoxy compound having the desired characteristics with stability tends to be difficult.

In this reaction, water is added to a solution prepared by dissolving an organoaluminum compound in a suitable organic solvent. In order to obtain the organic aluminoxy compound having the desired characteristics with stability, the process in which the temperature of the reaction system is controlled or the process in which the rate of addition of water is controlled is used. In the process in which the temperature of the reaction system is controlled, it is preferred that water is added while the temperature of the reaction system is kept at 0° C. or lower. The rate of addition of water is not particularly limited in this process. When the temperature of the reaction system is higher than 0° C. during addition of water in the process, the organic aluminoxy compound having the desired characteristics is sometimes not obtained with stability. The preferable temperature of the reaction system during addition of water is selected in the range of −5 to −80° C. for obtaining the organic aluminoxy compound having the desired characteristics efficiently with stability and also for achieving easier operation.

In the process in which the rate of addition of water is controlled, it is preferred that water is added at a rate of 0.1 mol/min or less per 1 mol of the organoaluminum compound. In this case, the temperature of the reaction system during addition of water is not particularly limited. When the rate of addition of water is more than 0.1 mol/min, the organic aluminoxy compound having the desired characteristics is sometimes not obtained with stability. The preferable rate of addition water is selected in the range of 0.001 to 0.1 mol/min per 1 mol of the organoaluminum compound for obtaining the organic aluminoxy compound having the desired characteristics efficiently with stability and also for practical application of the process.

As described above, when an organoaluminum compound is brought into reaction with water itself, the organic aluminoxy compound having the desired characteristic can be obtained efficiently without causing large dispersion in the characteristics by controlling both of the temperature of the reaction system and the rate of addition of water during addition of water, in other words, by adding water at a rate of 0.1 mol/min or less per 1 mol of the organoaluminum compound while the temperature of the reaction system is kept at 0° C. or lower. In order to obtain the organic aluminoxy compound having the desired characteristics efficiently with stability, it is particularly advantageous that the temperature of the reaction system during addition of water is in the range of −100 to 50° C., preferably in the range of −100 to 0° C., more preferably in the range of −80 to −5° C., and the rate of addition of water is in the range of 0.001 to 0.1 mol/min per 1 mol of the organoaluminum compound in view of practical application of the process, such as easiness and time of the operation. In this case, the temperature of the reaction system is not particularly limited in the reactions after the addition of water has been finished.

As the organic solvent used in the production of the organic aluminoxy compound of the present invention, for example, an inert solvent, such as an aliphatic or alicyclic hydrocarbon having 5 to 18 carbon atoms and an aromatic hydrocarbon having 6 to 20 carbon atoms, can be used. Specific examples of the organic solvent include n-pentane, isopentane, hexane, heptane, octane, nonane, decane, teteradecane, cyclohexane, benzene, toluene, xylene, and ethylbenzene. A single type or a combination of two or more types of the organic solvent can be used.

As the organoaluminum compound, a trialkylaluminum represented by the following general formula (I):

$$R^3Al \tag{I}$$

is generally used. In general formula (I), R preferably represents an alkyl group having 1 to 3 carbon atoms, specific examples of which include methyl group, ethyl group, and n-propyl group. The three R may be the same with each other or different from each other.

Preferable examples of the trialkylaluminum include trimethylaluminum, triethylaluminum, tri-n-propylaluminum, and triisopropylaluminum. A single type or a combination of two or more types of the trialkylaluminum can be used.

When the trialkylaluminum represented by general formula (I) is used as the organoaluminum compound, the organic aluminoxy compound obtained as the reaction product of the organoaluminum compound and water has one or more of the following structures.

Chain structures represented by the following general formula (IIa):

Branched chain structures represented by the following general formula (IIb):

Ring structures represented by the following general formula (III):

Cage structures formed by association of two or more molecules of aluminoxane. The cage structure may have various forms depending on the number of molecule of aluminoxane constituting the cage structure by association and the condition of association.

In above general formulae (IIa), (IIb), and (III), R is the same as that described above, t represents a number generally in the range of 2 to 50, preferably in the range of 3 to 30, more preferably in the range of 4 to 20, x, y, and z represent each an integer of 1 to 50, and x+y+z≧3. A plurality of R in a molecule may be the same with each other or different from each other. The branched chain structure represented by general formula (IIb) may be a branched chain structure having a plurality of branches.

Specific examples of the above reaction product of the organoaluminum compound and water include methylaluminoxane, ethylaluminoxane, n-propylaluminoxane, and isopropylaluminoxane.

The catalyst for producing a polymer of the present invention comprises (A) a transition metal, (B) organic aluminoxy compound (I) and/or (II) having the above specific characteristics, and optionally, a metal compound containing alkyl group.

As the transition metal compound of component (A), various types of compound can be used. Compounds represented by the following general formula (IV) or (V):

[wherein M represents a metal of any of Groups 3 to 10 of the Periodic Table or a metal of the lanthanoid group; $R^1$, $R^2$, $R^3$, and $R^4$ represent each an alkyl group, an alkoxy group, an alkylthio group, an aryl group, cyclopentadienyl group, a substituted cyclopentadienyl group, indenyl group, a substituted indenyl group, fluorenyl group, an amino group, an amido group, an acyloxy group, a phosphide group, a halogen atom, or a chelating ligand; a, b, and c represent each an integer of 0 to 4; d and e represent each an integer of 0 to 3; and any two members selected from $R^1$ to $R^4$ may be crosslinked to each other through $CH_2$, $Si(CH_3)_2$, or the like] are generally used.

As the above metal of any of Groups 3 to 10 of the Periodic Table or the above metal of the lanthanoid group, metals of Group 4, particularly titanium and hafnium, are preferably used.

As the titanium compound, various compounds can be used. For example, at least one type of compound selected from the titanium compounds represented by the following general formula (VI) or general formula (VII):

and chelate compounds of titanium can be used.

In general formulae (VI) and (VII), $R^5$, $R^6$, $R^7$, and $R^8$ represent each hydrogen atom, an alkyl group having 1 to 20 carbon atoms (such as methyl group, ethyl group, propyl group, butyl group, amyl group, isoamyl group, isobutyl group, octyl group, and 2-ethylhexyl group), an alkoxy group having 1 to 20 carbon atoms (such as methoxy group, ethoxy group, propoxy group, butoxy group, amyloxy group, hexyloxy group, and 2-ethylhexyloxy group), an aryl group, an alkylaryl group, or an arylalkyl group having 6 to 20 carbon atoms (such as phenyl group, tolyl group, xylyl group, and benzyl group), an aryloxy group having 6 to 20 carbon atoms (such as phenoxy group), an acyloxy group having 1 to 20 carbon atoms (such as acetoxy group, benzoyloxy group, butylcarbonyloxy group, and heptadecylcarbonyloxy group), an amino group having 1 to 50 carbon atoms (such as dimethylamino group, diethylamino group, diphenylamino group, and bistrimethylsilylamino group), an amido group (such as acetoamido group, ethylamido group, diphenylamido group, and methylphenylamido group), a phosphide group (such as dimethylphosphide group, diethylphosphide group, and diphenylphosphide group), cylcopentadienyl group, a substituted cyclopentadienyl group (such as methylcyclopentadienyl group, 1,2-dimethylcyclopentadienyl group, tetramethylcyclopentadienyl group, and pentamethylcyclopentadienyl group), indenyl group, a substituted indenyl group (such as methylindenyl group, dimethylindenyl group, tetramethylindenyl group, hexamethylindenyl group, and 4,5,6,7-tetrahydro-1, 2,3-trimethylindenyl group), a fluorenyl group (methylfluorenyl group, dimethylfluorenyl group, tetramethylfluorenyl group, and octamethylfluorenyl group), an alkylthio group (such as methylthio group, ethylthio group, butylthio group, amylthio group, isoamylthio group, isobutylthio group, octylthio group, and 2-ethylhexylthio group), an arylthio group (such as phenylthio group, p-methylphenylthio group, and p-methoxyphenylthio group), a chelating ligand (such as 2,2-thiobis(4-methyl-6-t-butylphenoxy) group), or a halogen atom (such as chlorine, bromine, iodine, and fluorine). $R^5$, $R^6$, $R^7$, and $R^8$ may be the same with each other or different from each other. Any two members selected from $R^5$, $R^6$, $R^7$, and $R^8$ may be crosslinked to each other through $CH_2$, $Si(CH_3)_2$, or the like. a, b, and c represent each an integer of 0 to 4, and d and e represent each an integer of 0 to 3.

Specific examples of the titanium compound include cyclopentadienyltrimethyltitanium, cyclopentadienyltriethyltitanium, cyclopentadienyltripropyltitanium, cyclopentadienyltributyltitanium, methylcyclopentadienyltrimethyltitanium, 1,2-dimethylcyclopentadienyltrimethyltitanium, 1,2,4-trimethylcyclopentadienyltrimethyltitanium, 1,2,3,4-tetramethylcyclopentadienyltrimethyltitanium, pentamethylcyclopentadienyltrimethyltitanium, pentamethylcyclopentadienyltriethyltitanium, pentamethylcyclopentadienyltripropyltitanium, pentamethylcyclopentadienyltributyltitanium, cyclopentadienylmethyltitanium dichloride, cyclopentadienylethyltitanium dichloride, pentamethylcyclopentadienylmethyltitanium dichloride, pentamethylcyclopentadienylethyltitanium dichloride, cyclopentadienyldimethyltitanium monochloride, cyclopentadienyldiethyltitanium monochloride, cyclopentadienyltitanium trimethoxide, cyclopentadienyltitanium triethoxide, cyclopentadienyltitanium tripropoxide, cyclopentadienyltitanium triphenoxide, pentamethylcyclopentadienyltitanium trimethoxide, pentamethylcyclopentadienyltitanium triethoxide, pentamethylcyclopentadienyltitanium tripropoxide, pentamethylcyclopentadienyltitanium tributoxide, pentamethylcyclopentadienyltitanium triphenoxide, cyclopentadienyltitanium trichloride, pentamethylcyclopentadienyltitanium trichloride, cyclopentadienylmethoxytitanium dichloride, cyclopentadienyldimethoxytitanium chloride, pentamethylcyclopentadienylmethoxytitanium dichloride, cyclopentadienyltribenzyltitanium, pentamethylcyclopentadienylmethyldiethoxytitanium, indenyltitanium trichloride, indenyltitanium trimethoxide, indenyltitanium triethoxide, indenyltrimethyltitanium, indenyltribenzyltitanium, (t-butylamido)dimethyl (tetramethyl-$\eta^5$-cyclopentadienyl)silanetitanium dichloride, (t-butylamido)dimethyl(tetramethyl-$\eta^5$-cyclopentadienyl) silanetitanium dimethyl, and (t-butylamido)dimethyl (tetramethyl-$\eta^5$-cyclopentadienyl)silanetitanium dimethoxide.

Moreover, a condensed titanium compound represented by the following general formula (VIII):

[wherein $R^9$ and $R^{10}$ represent each a halogen atom, an alkoxy group having 1 to 20 carbon atoms, or an acyloxy group, and k represents a number of 2 to 20] may also be used as the titanium compound. Complex compounds formed from the above titanium compounds and esters or ethers may also be used as the titanium compound.

Typical examples of the trivalent titanium compound represented by general formula (V) include titanium trihalides, such as titanium trichloride; cyclopentadienyltitanium compounds, such as cyclopentadienyltitanium dichloride; and compounds obtained by reduction of tetravalent titanium compounds. Complex compounds formed from the trivalent titanium compounds and esters or ethers may also be used.

Examples of the zirconium compound used as the transition metal compound include tetrabenzylzirconium, zirconium tetraethoxide, zirconium tetrabutoxide, bisindenylzirconium dichloride, triisopropoxyzirconium chloride, zirconium benzyl dichloride, and tributoxyzirconium chloride. Examples of the hafnium compound used as the transition metal compound include tetrabenzylhafnium, hafnium tetraethoxide, and hafnium tetrabutoxide.

Examples of the vanadium compound used as the transition metal compound include vanadyl bisacetylacetonate, vanadyl triacetylacetonate, triethoxyvanadyl, and tripropoxyvanadyl. Among these transition metal compounds, titanium compounds are preferable.

As the transition metal compound of component (A), a transition metal compound having two conjugated π-electronic ligands, such as a transition metal compound represented by the following general formula (IX):

$$M^1 R^{11} R^{12} R^{13} R^{14} \quad (IX)$$

can also be used.

In general formula (IX), $M^1$ represents titanium, hafnium, or zirconium. $R^{11}$ and $R^{12}$ represent each cyclopentadienyl group, a substituted cyclopentadienyl group (such as methylcyclopentadienyl group, 1,3-dimethylcyclopentadienyl group, 1,2,4-trimethylcyclopentadienyl group, 1,2,3,4-tetramethylcyclopentadienyl group, pentamethylcyclopentadienyl group, tirmethylsilylcyclopentadienyl group, 1,3-di(trimethylsilyl)cyclopentadienyl group, 1,2,4-tri(trimethylsilyl)cyclopentadienyl group, tertiary-butylcyclopentadienyl group, 1,3-di(tertiary-butyl)cyclopentadienyl group, and 1,2,4-tri(tertiary-butyl)cyclopentadienyl group), indenyl group, a substituted indenyl group (such as methylindenyl group, dimethylindenyl group, and trimethylindenyl group), fluorenyl group, or a substituted fluorenyl group (such as methylfluorenyl group). $R^{11}$ and $R^{12}$ may be the same or different. $R^{11}$ and $R^{12}$ may have a structure in which $R^{11}$ and $R^{12}$ are crosslinked to each other through an alkylidene group having 1 to 5 carbon atoms (such as methine group, ethylidene group, propylidene group, and dimethylcarbyl group), or an alkylsilylene group having 1 to 20 carbon atoms and 1 to 5 silicon atoms (such as dimethylsilylene group, diethylsilylene group, and dibenzylsilylene group). $R^{13}$ and $R^{14}$ represent each hydrogen atom, a halogen atom (such as chlorine, bromine, iodine, and fluorine), an alkyl group having 1 to 20 carbon atoms (such as methyl group, ethyl group, propyl group, n-butyl group, isobutyl group, amyl group, isoamyl group, octyl group, and 2-ethylhexyl group), an aryl group having 6 to 20 carbon atoms (such as phenyl group and naphthyl group), an arylalkyl group having 7 to 20 carbon atoms (such as benzyl group), an alkoxy group having 1 to 20 carbon atoms (such as methoxy group, ethoxy group, propoxy group, butoxy group, amyloxy group, hexyloxy group, octyloxy group, and 2-ethylhexyloxy group), an aryloxy group having 6 to 20 carbon atoms (such as phenoxy group), an amino group, or a thioalkoxy group having 1 to 20 carbon atoms. $R^{13}$ and $R^{14}$ may be the same or different and may be crosslinked to each other through a hydrocarbon group having 1 to 5 carbon atoms, an alkylsilylene group having 1 to 20 carbon atoms and 1 to 5 silicon atoms, or a hydrocarbon group containing germanium which has 1 to 20 carbon atoms and 1 to 5 germanium atoms.

Specific examples of the transition metal compound represented by general formula (IX) include biscyclopentadienyltitanium dimethyl, biscyclopentadienyltitanium diethyl, biscyclopentadienyltitanium dipropyl, biscyclopentadienyltitanium dibutyl, bis(methylcyclopentadienyl)titanium dimethyl, bis(tertiary-butylcyclopentadienyl)titanium dimethyl, bis(1,3-dimethylcyclopentadienyl)titanium dimethyl, bis(1,3-di-tertiary-butylcyclopentadienyl)titanium dimethyl, bis(1,2,4-trimethylcyclopentadienyl)titanium dimethyl, bis(1,2,3,4-tetramethylcyclopentadienyl)titanium dimethyl, biscyclopentadienyltitanium dimethyl, bis(trimethylsilylcyclopentadienyl)titanium dimethyl, bis(1,3-di(trimethylsilyl)cyclopentadienyl)titanium dimethyl, bis(1, 2,4-tris(trimethylsilyl)cyclopentadienyl)titanium dimethyl, bisindenyltitanium dimethyl, bisfluorenyltitanium dimethyl, methylenebiscyclopentadienyltitanium dimethyl, ethylidenebiscyclopentadienyltitanium dimethyl, methylenebis(2,3,4,5-tetramethylcyclopentadienyl)titanium dimethyl, ethylidenebis(2,3,4,5-tetramethylcyclopentadienyl)titanium dimethyl, dimethysilylenebis(2,3,4,5-tetramethylcyclopentadienyl)titanium dimethyl, methylenebisindenyltitanium dimethyl, ethylidenebisindenyltitanium dimethyl, dimethylsilylenebisindenyltitanium dimethyl, methylenebisfluorenyltitanium dimethyl, ethylidenebisfluorenyltitanium dimethyl, dimethylsilylenebisfluorenyltitanium dimethyl, methylene(tertiary-butylcyclopentadienyl)(cyclopentadienyl)titanium dimethyl, methylene(cyclopentadienyl)(indenyl)titanium dimethyl, ethylidene(cyclopentadienyl)(indenyl)titanium dimethyl, dimethylsilylene(cyclopentadienyl)(indenyl)titanium dimethyl, methylene(cyclopentadienyl)(fluorenyl)titanium dimethyl, ethylidene(cyclopentadienyl)(fluorenyl)titanium dimethyl, dimethylsilylene(cyclopentadienyl)(fluorenyl)titanium dimethyl, methylene(indenyl)(fluorenyl)titanium dimethyl, ethylidene(indenyl)(fluorenyl)titanium dimethyl, dimethylsilylene(indenyl)(fluorenyl)titanium dimethyl, biscyclopentadienyltitanium dibenzyl, bis(tertiary-butylcyclopentadienyl)titanium dibenzyl, bis(methylcyclopentadienyl)titanium dibenzyl, bis(1,3-dimethylcyclopentadienyl)titanium dibenzyl, bis(1,2,4-trimethylcyclopentadienyl)titanium dibenzyl, bis(1,2,3,4-tetramethylcyclopentadienyl)titanium dibenzyl, bispentamethylcyclopentadienyltitanium dibenzyl, bis(trimethylsilylcyclopentadienyl)titanium dibenzyl, bis(1,3-di(trimethylsilyl)cyclopentadienyl)titanium dibenzyl, bis(1, 2,4-tris(trimethylsilyl)cyclopentadienyl)titanium dibenzyl, bisindenyltitanium dibenzyl, bisfluorenyltitanium dibenzyl, methylenebiscyclopentadienyltitanium dibenzyl, ethylidenebiscyclopentadienyltitanium dibenzyl, methylenebis(2,3,4,5-tetramethylcyclopentadienyl)titanium dibenzyl, ethylidenebis(2,3,4,5-tetramethylcyclopentadienyl)titanium dibenzyl, dimethylsilylenebis(2,3,4,5-tetramethylcyclopentadienyl)titanium dibenzyl, methylenebisindenyltitanium dibenzyl, ethylidenebisindenyltitanium dibenzyl, dimethylsilylenebisindenyltitanium dibenzyl, methylenebisfluorenyltitanium dibenzyl, ethylidenebisfluorenyltitanium dibenzyl, dimethylsilylenebisfluorenyltitanium dibenzyl, methylene(cyclopentadienyl)(indenyl)titanium dibenzyl, ethylidene(cyclopentadienyl)(indenyl)titanium dibenzyl, dimethylsilylene(cyclopentadienyl)(indenyl)titanium dibenzyl, methylene(cyclopentadienyl)(fluorenyl)titanium dibenzyl, ethylidene(cyclopentadienyl)(fluorenyl)titanium dibenzyl, dimethylsilylene(cyclopentadienyl)(fluorenyl)titanium dibenzyl, methylene(indenyl)(fluorenyl)titanium dibenzyl, ethylidene(indenyl)(fluorenyl)titanium dibenzyl, dimethylsilylene(indenyl)(fluorenyl)titanium dibenzyl, biscyclopentadienyltitanium dimethoxide, biscyclopentadienyltitanium diethoxide, biscyclopentadienyltitanium dipropoxide, biscyclopentadienyltitanium dibutoxide, biscyclopentadienyltitanium diphenoxide, bis(methylcyclopentadienyl)titanium dimethoxide, bis(1,3-dimethylcyclopentadienyl)titanium dimethoxide, bis(1,2,4-trimethylcyclopentadienyl)titanium dimethoxide, bis(1,2,3,4-tetramethylcyclopentadienyl)titanium dimethoxide, bispentamethylcyclopentadienyltitanium dimethoxide, bis(trimethylsilylcyclopentadienyl)titanium dimethoxide, bis(1,3-di(trimethylsilyl)cyclopentadienyl)titanium dimethoxide, bis(1,2,4-tris(trimethyl silyl)cyclopentadienyl)titanium dimethoxide, bisindenyltitanium dimethoxide, bisfluorenyltitanium dimethoxide, methylenebiscyclopentadienyltitanium dimethoxide, ethylidenebiscyclopentadienyltitanium dimethoxide, methylenebis(2,3,4,5-tetramethylcyclopentadienyl)titanium dimethoxide, ethylidenebis(2,3,4,5-tetramethylcyclopentadienyl)titanium dimethoxide, dimethylsilylenebis(2,3,4,5-tetramethylcyclopentadienyl) titanium dimethoxide, methylenebisindenyltitanium dimethoxide, methylenebis(methylindenyl)titanium dimethoxide, ethylidenebisindenyltitanium dimethoxide, dimethylsilylenebisindenyltitanium dimethoxide, methylenebisfluorenyltitanium dimethoxide, methylenebis(methylfluorenyl)titanium dimethoxide, ethylidenebisfluorenyltitanium dimethoxide, dimethylsilylenebisfluorenyltitanium dimethoxide, methylene(cyclopentadienyl)(indenyl)titanium dimethoxide, ethylidene(cyclopentadienyl)(indenyl) titanium dimethoxide, dimethylsilylene(cyclopentadienyl) (indenyl)titanium dimethoxide, methylene (cyclopentadienyl)(fluorenyl)titanium dimethoxide, ethylidene(cyclopentadienyl)(fluorenyl)titanium dimethoxide, dimethylsilylene(cyclopentadienyl)(fluorenyl) titanium dimethoxide, methylene(indenyl)(fluorenyl) titanium dimethoxide, ethylidene(indenyl)(fluorenyl) titanium dimethoxide, and dimethylsilylene(indenyl) (fluorenyl)titanium dimethoxide.

Examples of the zirconium compound include ethylidenebiscyclopentadienylzirconium dimethoxide and dimethylsilylenebiscyclopentadienylzirconium dimethoxide. Examples of the hafnium compound include ethylidenebiscyclopentadienylhafnium dimethoxide and dimethylsilylenebiscyclopentadienylhafnium dimethoxide. Among these compounds, the titanium compounds are particularly preferable.

Specific examples of the transition metal compound further include bidentate coordinated complex compounds, such as 2,2'-thiobis(4-methyl-6-t-butylphenoxy)titanium isopropoxide and 2,2'-thiobis(4-methyl-6-t-butylphenoxy) titanium dimethoxide.

Still further examples of the transition metal of component (A) include transition metal compounds having the structure represented by the following general formula (X):

$$R'MX'_{p-1}L_q \quad (X)$$

In general formula (X), R' represents a π-electronic ligand which is a condensed polycyclic cyclopentadienyl group having a polycyclic structure in which cyclopentadienyl groups are bonded to each other by condensation in the form of a polycyclic structure and at least one of the rings in the polycyclic structure is a saturated ring. Examples of the condensed polycyclic cyclopentadienyl group include groups represented by the following general formulae (XI) to (XIII):

(XI)

(XII)

(XIII)

[wherein $R^{15}$, $R^{16}$, and $R^{17}$ represent each hydrogen atom, a halogen atom, an aliphatic hydrocarbon group having 1 to 20 carbon atoms, an aromatic hydrocarbon group having 6 to 20 carbon atoms, an alkoxy group having 1 to 20 carbon atoms, an aryloxy group having 6 to 20 carbon atoms, a thioalkoxy group having 1 to 20 carbon atoms, a thioaryloxy group having 6 to 20 carbon atoms, an amino group, an amido group, carboxyl group, or an alkylsilyl group, and may be the same with each other or different from each other; and w, x, y, and z represent each an integer of 1 or more]. Among these groups, 4,5,6,7-tetrahydroindenyl groups are preferable because of higher catalyst activity and easier preparation.

Specific examples of R' include 4,5,6,7-tetrahydroindenyl group, 1-methyl-4,5,6,7-tetrahydroindenyl group, 2-methyl-4,5,6,7-tetrahydroindenyl group, 1,2-dimethyl-4,5,6,7-tetrahydroindenyl group, 1,3-dimethyl-4,5,6,7-tetrahydroindenyl group, 1,2,3-trimethyl-4,5,6,7-tetrahydroindenyl group, 1,2,3,4,5,6,7-heptamethyl-4,5,6,7-tetrahydroindenyl group, 1,2,4,5,6,7-hexamethyl-4,5,6,7-tetrahydroindenyl group, 1,3,4,5,6,7-hexamethyl-4,5,6,7-tetrahydroindenyl group, octahydrofluorenyl group, 1,2,3,4-tetrahydrofluorenyl group, 9-methyl-1,2,3,4-tetrahydrofluorenyl group, and 9-methyloctahydrofluorenyl group.

M represents a metal of any of Groups 3 to 6 of the Periodic Table or a metal of the lanthanoid group, such as titanium, zirconium, hafnium, metals of the lanthanoid group, niobium, and tantalum. Among these metals, titanium is preferable in view of the catalyst activity. X' represents a σ-ligand. Specific examples of the group represented by X' include hydrogen atom, a halogen atom, an aliphatic hydrocarbon group having 1 to 20 carbon atoms, an aromatic hydrocarbon group having 6 to 20 carbon atoms, an alkoxy group having 1 to 20 carbon atoms, an aryloxy group having 6 to 20 carbon atoms, a thioalkoxy group having 1 to 20 carbon atoms, a thioaryloxy group having 6 to 20 carbon atoms, an amino group, an amido group, carboxyl group, and an alkylsilyl group. A plurality of groups represented by X' may be the same with each other or different from each other and may be bonded to each other through any group.

More specific examples of the group represented by X' include hydrogen atom, chlorine atom, bromine atom, iodine atom, methyl group, benzyl group, phenyl group, trimethylsilylmethyl group, methoxy group, ethoxy group, phenoxy group, thiomethoxy group, thiophenoxy group, dimethylamino group, and diisopropylamino group. A plurality of groups represented by X' may be the same with each other or different from each other and may be bonded to each other through any group. L represents a Lewis base, p represents the valency of the metal represented by M, and q represents 0, 1, or 2. When a plurality of the Lewis bases represented by L are present, the plurality of Lewis bases may be the same with each other or different from each other.

Examples of the transition metal compound represented by general formula (X) include 4,5,6,7-tetrahydroindenyltitanium trichloride, 4,5,6,7-tetrahydroindenyltitanium trimethyl, 4,5,6,7-tetrahydroindenyltitanium tribenzyl, 4,5,6,7-tetrahydroindenyltitanium trimethoxide, 1-methyl-4,5,6,7-tetrahydroindenyltitanium trichloride, 1-methyl-4,5,6,7-tetrahydroindenyltitanium trimethyl, 1-methyl-4,5,6,7-tetrahydroindenyltitanium tribenzyl, 1-methyl-4,5,6,7-tetrahydroindenyltitanium trimethoxide, 2-methyl-4,5,6,7-tetrahydroindenyltitanium trichloride, 2-methyl-4,5,6,7-tetrahydroindenyltitanium trimethyl, 2-methyl-4,5,6,7-tetrahydroindenyltitanium tribenzyl, 2-methyl-4,5,6,7-tetrahydroindenyltitanium trimethoxide, 1,2-dimethyl-4,5,6,7-tetrahydroindenyltitanium trichloride, 1,2-dimethyl-4,5,6,7-tetrahydroindenyltitanium trimethyl, 1,2-dimethyl-4,5,6,7-tetrahydroindenyltitanium tribenzyl, 1,2-dimethyl-4,5,6,7-tetrahydroindenyltitanium trimethoxide, 1,3-dimethyl-4,5,6,7-tetrahydroindenyltitanium trichloride, 1,3-dimethyl-4,5,6,7-tetrahydroindenyltitanium trimethyl, 1,3-dimethyl-4,5,6,7-tetrahydroindenyltitanium tribenzyl, 1,3-dimethyl-4,5,6,7-tetrahydroindenyltitanium trimethoxide, 1,2,3-trimethyl-4,5,6,7-tetrahydroindenyltitanium trichloride, 1,2,3-trimethyl-4,5,6,7-tetrahydroindenyltitanium trimethyl, 1,2,3-trimethyl-4,5,6,7-tetrahydroindenyltitanium tribenzyl, 1,2,3-trimethyl-4,5,6,7-tetrahydroindenyltitanium trimethoxide, 1,2,3,4,5,6,7-heptamethyl-4,5,6,7-tetrahydroindenyltitanium trichloride, 1,2,3,4,5,6,7-heptamethyl-4,5,6,7-tetrahydroindenyltitanium trimethyl, 1,2,3,4,5,6,7-heptamethyl-4,5,6,7-tetrahydroindenyltitanium tribenzyl, 1,2,3,4,5,6,7-heptamethyl-4,5,6,7-tetrahydroindenyltitanium trimethoxide, 1,2,4,5,6,7-hexamethyl-4,5,6,7-tetrahydroindenyltitanium trichloride, 1,2,4,5,6,7-hexamethyl-4,5,6,7-tetrahydroindenyltitanium trimethyl, 1,2,4,5,6,7-hexamethyl-4,5,6,7-tetrahydroindenyltitanium tribenzyl, 1,2,4,5,6,7-hexamethyl-4,5,6,7-tetrahydroindenyltitanium trimethoxide, 1,3,4,5,6,7-hexamethyl-4,5,6,7-tetrahydroindenyltitanium trichloride, 1,3,4,5,6,7-hexamethyl-4,5,6,7-tetrahydroindenyltitanium trimethyl, 1,3,4,5,6,7-hexamethyl-4,5,6,7-tetrahydroindenyltitanium tribenzyl, 1,3,4,5,6,7-hexamethyl-4,5,6,7-tetrahydroindenyltitanium trimethoxide, octahydrofluorenyltitanium trichloride, octahydrofluorenyltitanium trimethyl, octahydrofluorenyltitanium tribenzyl, octahydrofluorenyltitanium trimethoxide, 1,2,3,4-tetrahydrofluorenyltitanium trichloride, 1,2,3,4-tetrahydrofluorenyltitanium trimethyl, 1,2,3,4-tetrahydrofluorenyltitanium tribenzyl, 1,2,3,4-tetrahydrofluorenyltitanium trimethoxide, 9-methyl-1,2,3,4-tetrahydrofluorenyltitanium trichloride, 9-methyl-1,2,3,4-tetrahydrofluorenyltitanium trimethyl, 9-methyl-1,2,3,4-tetrahydrofluorenyltitanium tribenzyl, 9-methyl-1,2,3,4-tetrahydrofluorenyltitanium trimethoxide, 9-methyl-octahydrofluorenyltitanium trichloride, 9-methyl-octahydrofluorenyltitanium trimethyl, 9-methyl-octahydrofluorenyltitanium tribenzyl, 9-methyl-octahydrofluorenyltitanium trimethoxide, compounds obtained by replacing titanium in the above compounds with zirconium or hafnium, and similar compounds containing a metal of another group of the Periodic Table or a metal of the lanthanoid group. Of course, the transition metal compound is not limited to the above compounds. Among these compounds, titanium compounds are preferable in view of the catalyst activity.

In the present invention, a single type or a combination of two or more type of the transition metal compound of component (A) can be used.

In the catalyst for producing a polymer of the present invention, organic aluminoxy compound I or II having the specific characteristics described above is used as component (B). A single type or a combination of two or more types of the organic aluminoxy compound can be used as component (B). The organic aluminoxy compound may also be used as component (B) in combination with an ionic compound which can form an ionic complex compound by reaction with the above transition metal compound of component (A) and is optionally used.

As the ionic compound which can form an ionic complex compound by reaction with the transition metal compound of component (A) and is optionally used, coordinated complex compounds composed of an anion in which a plurality of groups are bonded to a metal and a cation can be used. As the coordinated complex compound composed of an anion in which a plurality of groups are bonded to a metal and a cation, various compounds can be used. For example, a compound represented by the following general formula (XIV) or (XV):

can advantageously be used. In above general formulae (XIV) and (XV), $L^2$ represents $M^4$, $R^{18}R^{19}M^5$, or $R^{20}_3C$ which are described below; $L^1$ represents a Lewis base; $M^2$ and $M^3$ represent each a metal selected from the elements of Groups 5 to 15 of the Periodic Table; $M^4$ represents a metal selected from the elements of Groups 8 to 12 of the Periodic Table; $M^5$ represents a metal selected from the elements of Group 8 to 10 of the Periodic Table; $X^1$ to $X^n$ represent each hydrogen atom, a dialkylamino group, an alkoxy group, an aryloxy group, an alkyl group having 1 to 20 carbon atoms, an aryl group, an alkylaryl group, or an arylalkyl group having 6 to 20 carbon atoms, a substituted alkyl group, an organometalloid group, or a halogen atom; $R^{18}$ and $R^{19}$ represent each cyclopentadienyl group, a substituted cyclopentadienyl group, indenyl group, or fluorenyl group; $R^{20}$ represents an alkyl group; m represents the valency of $M^2$ or $M^3$ which is an integer of 1 to 7; n represents an integer of 2 to 8; g is the ionic valency of $L^1$–H or $L^2$ which is an integer of 1 to 7; h is an integer of 1 or more; and i=h×g/(n−m).

Specific examples of $M^2$ and $M^3$ include atoms of B, Al, C, Si, P, As, and Sb. Specific examples of $M^4$ include atoms of Ag and Cu. Specific examples of $M^5$ include atoms of Fe, Co, and Ni. Specific examples of $X^1$ to $X^n$ include dialkylamino groups, such as dimethylamino group and diethylamino group; alkoxy groups, such as methoxy group, ethoxy group, and n-butoxy group; aryloxy groups, such as phenoxy group, 2,6-dimethylphenoxy group, and naphthyloxy group; alkyl groups having 1 to 20 carbon atoms, such as methyl group, ethyl group, n-propyl group, isopropyl group, n-butyl group, n-octyl group, and 2-ethylhexyl group; aryl groups, alkylaryl groups, and arylalkyl groups having 6 to 20 carbon atoms, such as phenyl group, p-tolyl group, benzyl group, pentafluorophenyl group, 3,5-di (trifluoromethyl)phenyl group, 4-tertiary-butylphenyl group, 2,6-dimethylphenyl group, 3,5-dimethylphenyl group, 2,4-dimethylphenyl group, and 1,2-dimethylphenyl group; halogens, such as F, Cl, Br, and I; and organometalloid groups, such as pentamethylstibine group, trimethylsilyl group, trimethylgermyl group, diphenylarsine group, dicyclohexylstibine group, and diphenylboron group. Specific examples of the substituted cyclopentadienyl group represented by each of $R^{18}$ and $R^{19}$ include methylcyclopentadienyl group, butylcyclopentadienyl group, and pentamethylcyclopentadienyl group.

Specific examples of the anion in which a plurality of groups are bonded to a metal include $B(C_6F_5)_4-$, $B(C_6HF_4)_4-$, $B(C_6H_2F_3)_4-$, $B(C_6H_3F_2)_4-$, $B(C_6H_4F)_4-$, $B(C_6CF_3F_4)_4-$, $B(C_6H_5)_4-$, $BF_4-$, $PF_6-$, $P(C_6F_5)_6-$, and $Al(C_6HF_4)_4-$. Specific examples of the cation include metal cations, such as $Cp_2Fe^+$, $(MeCp)_2Fe^+$, $(tBuCp)_2Fe^+$, $(Me_2Cp)_2Fe^+$, $(Me_3Cp)_2Fe^+$, $(Me_4Cp)_2Fe^+$, $(Me_5Cp)_2Fe^+$, $Ag^+$, $Na^+$, and $Li^+$; ions containing nitrogen, such as pyridinium ion, 2,4-dinitro-N,N-diethylanilinium ion, diphenylammonium ion, p-nitroanilinium ion, 2,5-dichloroanilinium ion, p-nitro-N, N-dimethylanilinium ion, quinolinium ion, N,N-dimethylanilinium ion, and N,N-diethylanilinium ion; carbenium compounds, such as triphenylcarbenium ion, tri(4-methylphenyl)carbenium ion, and tri(4-methoxyphenyl) carbenium ion; alkylphosphonium ions, such as $CH_3PH_3^+$, $C_2H_5PH_3^+$, $C_3H_7PH_3^+$, $(CH_3)_2PH_2^+$, $(C_2H_5)_2PH_2^+$, $(C_3H_7)_2PH_2^+$, $(CH_3)_3PH^+$, $(C_2H_5)_3PH^+$, $(C_3H_7)_3PH^+$, $(CF_3)_3PH^+$, $(CH_3)_4P^+$, $(C_2H_5)_4P^+$, and $(C_3H_7)_4P^+$; and arylphosphonium ions, such as $C_6H_5PH_3^+$, $(C_6H_5)_2PH_2^+$, $(C_6H_5)_3PH^+$, $(C_6H_5)_4P^+$, $(C_2H_5)_2(C_6H_5)PH^+$, $(CH_3)(C_6H_5)PH_2^+$, $(CH_3)_2(C_6H_5)PH^+$, and $(C_2H_5)_2(C_6H_5)_2P^+$.

More specifically, among the compounds represented by general formulae (XIV) and (XV), the following compounds are preferably used. Preferable examples of the compound represented by general formula (XIV) include triethylammonium tetraphenyl borate, tri(n-butyl)ammonium tetraphenyl borate, trimethylammonium tetraphenyl borate, triethylammonium tetrakis(pentafluorophenyl) borate, tri(n-butyl) ammonium tetrakis(pentafluorophenyl) borate, and triethylammonium hexafluoroarsenate. Preferable examples of the compound represented by general formula (XV) include pyridinium tetrakis(pentafluorophenyl) borate, pyrrolinium tetrakis(pentafluorophenyl) borate, N-dimethylanilinium tetrakis(pentafluorophenyl) borate, methyldiphenylammonium tetrakis(pentafluorophenyl) borate, ferrocenium tetraphenyl borate, dimethylferrocenium tetrakis(pentafluorophenyl) borate, ferrocenium tetrakis(pentafluorophenyl) borate, decamethylferrocenium tetrakis(pentafluorophenyl) borate, acetylferrocenium tetrakis(pentafluorophenyl) borate, formylferrocenium tetrakis(pentafluorophenyl) borate, cyanoferrocenium tetrakis(pentafluorophenyl) borate, silver tetraphenyl borate, silver tetrakis(pentafluorophenyl) borate, trityl tetraphenyl borate, trityl tetrakis(pentafluorophenyl) borate, silver hexafluoroarsenate, silver hexafluoroantimonate, and silver tetrafluoroborate.

A single type or a combination of two or more types of the ionic compound can be used.

In the catalyst for producing a polymer of the present invention, a metal compound containing alkyl group can optionally be used as component (C). As the metal compound containing alkyl group, various compounds can be used. For example, an aluminum compound containing alkyl group represented by the following general formula (XVI):

$$R^{21}{}_u Al(OR^{22})_v E_{3-u-v} \qquad (XVI)$$

[wherein $R^{21}$ and $R^{22}$ represent each an alkyl group having 1 to 8 carbon atoms, preferably 1 to 4 carbon atoms, E represents hydrogen atom or a halogen atom, u represents a number in the range of $0<x\leq3$, preferably 2 or 3, most preferably 3, and v represents a number in the range of $0\leq v<3$, preferably 0 or 1]; a magnesium compound containing alkyl group represented by the following general formula (XVII):

$$R^{21}{}_2 Mg \qquad (XVII)$$

[wherein $R^{21}$ is the same as that described above]; or a zinc compound containing alkyl group represented by the following general formula (XVII):

$$R^{21}{}_2 Zn \qquad (XVII)$$

[wherein $R^{21}$ is the same as that described above] may be used.

Among the metal compounds containing alkyl group described above, aluminum compounds containing alkyl group, particularly trialkylaluminums and dialkylaluminum compounds, are preferable. Specific examples of the metal compounds containing alkyl group include trialkylaluminums, such as trimethylaluminum, triethylaluminum, tri-n-propylaluminum, triisopropylaluminum, tri-n-butylaluminum, triisobutylaluminum, and tri-t-butylaluminum; dialkylaluminum halides, such as dimethylaluminum chloride, diethylaluminum chloride, di-n-propylaluminum chloride, diisopropylaluminum chloride, di-n-butylaluminum chloride, diisobutylaluminum chloride, and di-t-butylaluminum chloride; dialkylaluminum alkoxides, such as dimethylaluminum methoxide, and dimethylaluminum ethoxide; and dialkylaluminum hydrides, such as dimethylaluminum hydride, diethylaluminum hydride, and diisobutylaluminum hydride. Further examples of the metal compound containing alkyl group include dialkylmagnesiums, such as dimethylmagnesium, diethylmagnesium, di-n-propylmagnesium, and diisopropylmagnesium; and dialkylzincs, such as dimethylzinc, diethylzinc, di-n-propylzinc, and diisopropylzinc.

A single type or a combination of two or more types of the metal compound containing alkyl group of component (C) may be used.

The process for preparing the catalyst for producing a polymer of the present invention is not particularly limited. For example, when a catalyst comprising components (A), (B), and (C) is prepared, (1) a process in which component (A) and component (B) are brought into contact with each other, and component (C) is added to the obtained product; (2) a process in which component (A) and component (C) are brought into contact with each other, and component (B) is added to the obtained product; (3) a process in which component (B) and component (C) are brought into contact with each other, and component (A) is added to the obtained product; or (4) a process in which component (A), component (B), and component (C) are simultaneously brought into contact with each other; each in a suitable organic solvent, may be used. The components can naturally be brought into contact with each other at the temperature of polymerization. It is also possible that the components are brought into contact with each other at a temperature of 0 to 100° C.

As the organic solvent used for preparing the catalyst for producing a polymer of the present invention, for example, an inert solvent, such as an aliphatic or alicyclic hydrocarbon having 5 to 18 carbon atoms and an aromatic hydrocarbon having 6 to 20 carbon atoms, can be used. Specific examples of the organic solvent include n-pentane, isopentane, hexane, heptane, octane, nonane, decane, tetradecane, cyclohexane, benzene, toluene, xylene, and ethylbenzene. A single type or a combination of two or more types of the organic solvent can be used. A monomer used for the polymerization may also be used as the organic solvent when a suitable type of the monomer is selected.

The catalyst for producing a polymer of the present invention obtained as described above is used for polymerizing a polymerizable unsaturated compound. The polymerizable unsaturated compound is not particularly limited as long as the polymerizable unsaturated compound can be polymerized by the above catalyst for producing a polymer. Examples of the polymerizable unsaturated compound include olefins, cyclic olefins, cyclic diolefins, chain conjugated diolefins, chain non-conjugated diolefins, aromatic vinyl compounds, and alkynes.

Examples of the olefin include $\alpha$-olefins, such as ethylene, propylene, butene-1, pentene-1, hexene-1, heptene-1, octene-1, nonene-1, decene-1, 4-phenylbutene-1, 6-phenylhexene-1, 3-methylbutene-1, 4-methylpentene-1, 3-methylpentene-1, 3-methylhexene-1, 4-methylhexene-1, 5-methylhexene-1, 3,3-dimethylpentene-1, 3,4-dimethylpentene-1, 4,4-dimethylpentene-1, 3,5,5-trimethylhexene-1, and vinylcyclohexene; and $\alpha$-olefins substituted with halogens, such as hexafluoropropene, tetrafluoroethylene, 2-fluoropropene, fluoroethylene, 1,1-difluoroethylene, 3-fluoropropene, trifluoroethylene, and 3,4-dichlorobutene-1.

Examples of the cyclic olefin include cyclopentene, cyclohexene, norbornene, 5-methylnorbornene, 5-ethylnorbornene, 5-propylnorbornene, 5,6-dimethylnorbornene, 1-methylnorbornene, 7-methylnorbornene, 5,5,6-trimethylnorbornene, 5-phenylnorbornene, and 5-benzylnorbronene. Examples of the cyclic diolefin include 5-ethylidenenorbornene, 5-vinylnorbornene, and dicyclopentadiene, norbornadiene.

Examples of the chain conjugated diolefin include 1,3-butadiene, and isoprene. Examples of the chain non-conjugated diolefin include 1,4-dienes, such as 1,4-hexadiene, 4-methyl-1,4-hexadiene, 5-methyl-1,4-hexadiene, and 5-methyl-1,4-heptadiene; 1,5-dienes, such as 1,5-hexadiene, 3-methyl-1,5-hexadiene, 3-ethyl-1,5-hexadiene, 3,4-dimethyl-1,5-hexadiene, 1,5-heptadiene, 5-methyl-1,5-heptadiene, 6-methyl-1,5-heptadiene, 1,5-octadiene, 5-methyl-1,5-octadiene, 6-methyl-1,5-octadiene, and 6-methyl-1,5-octadiene; 1,6-dienes, such as 1,6-octadiene, 6-methyl-1,6-octadiene, 7-methyl-1,6-octadiene, 7-ethyl-1,6-octadiene, 1,6-nonadiene, 7-methyl-1,6-nonadiene, and 4-methyl-1,6-nonadiene; 1,7-dienes, such as 1,7-octadiene, 3-methyl-1,7-octadiene, 3-ethyl-1,7-octadiene, 3,4-dimethyl-1,7-octadiene, 3,5-dimethyl-1,7-octadiene, 1,7-nonadiene, and 8-methyl-1,7-nonadiene; 1,11-dodecadiene; and 1,13-tetradecadiene.

Examples of the aromatic vinyl compound include styrene; $\alpha$-methylstyrene; alkyl- or arylstyrenes, such as p-methylstyrene, m-methylstyrene, o-methylstyrene, p-t-butylstyrene, and p-phenylstyrene; alkoxystyrenes, such as p-methoxystyrene, m-methoxystyrene, p-ethoxystyrene, p-n-propoxystyrene, and p-n-butoxystyrene; halogenated styrenes, such as p-chlorostyrene, p-bromostyrene, and p-iodostyrene; silylstyrenes containing alkyl groups or aryl groups, such as p-trimethylsilylstyrene, m-trimethylsilylstyrene, o-trimethylsilylstyrene, p-dimethylphenylsilylstyrene, p-methyldiphenylsilylstyrene, and p-triphenylsilylstyrene; silylstyrenes containing halogens, such as p-dimethylchlorosilylstrene, p-methyldichlorosilylstyrene, and p-trichlorosilylstyrene; alkenylstyrenes, such as p-(2-propenyl)styrene, m-(2-propenyl)styrene, p-(3-butenyl)styrene, m-(3-butenyl)styrene, o-(3-butenyl)styrene, and p-(3-butenyl)-$\alpha$-methylstyrene; vinylbiphenyls, such as 4-vinylbiphenyl, 3-vinylbiphenyl, and 2-vinylbiphenyl; vinylphenylnaphthalenes, such as 1-(4-vinylphenyl)naphthalene and 2-(3-vinylphenyl)naphthalene; vinylphenylanthracenes, such as 1-(4-vinylphenyl)anthracene and 2-(4-vinylphenyl)anthracene; vinylphenylphenanthrenes, such as 1-(4-vinylphenyl)phenanthrene and 2-(4-vinylphenyl)phenanthrene; and vinylphenylpyrenes, such as 1-(4-vinylphenyl)pyrene and 2-(4-vinylphenyl)pyrene.

Examples of the alkyne include acetylene and phenylacetylene.

A single type or a combination of two or more types of the polymerizable unsaturated compound can be used.

The process for polymerizing the above polymerizable unsaturated compound by using the catalyst for producing a polymer of the present invention is not particularly limited. Any process for polymerization, such as the slurry polymerization, the high temperature solution polymerization, the gas phase polymerization, the bulk polymerization, and the suspension polymerization, can be used.

When a solvent is used for the polymerization, an inert solvent, such as an aliphatic or alicyclic hydrocarbon having 5 to 18 carbon atoms and an aromatic hydrocarbon having 6 to 20 carbon atoms, can be used as the solvent. Specific examples of the solvent include n-pentane, isopentane, hexane, heptane, octane, nonane, decane, tetradecane, cyclohexane, benzene, toluene, xylene, and ethylbenzene. A single type or a combination of two or more types of the solvent can be used. A monomer used for the polymerization may also be used when a suitable type is selected.

The temperature of the polymerization is not particularly limited and selected generally in the range of 0 to 350° C., preferably in the range of 20 to 250° C. The pressure of the polymerization is not particularly limited either and selected generally in the range of 0 to 150 kg/cm$^2$G, preferably in the range of 0 to 100 kg/cm$^2$G. As the method of controlling the molecular weight of the polymer, suitable selection of the types and the amounts of the catalyst components, suitable selection of the temperature of polymerization, and introduction of hydrogen can be used.

The present invention is described in more detail in the following with reference to the examples. However, the present invention is not limited by the examples.

The $A_1/A_2$ ratio of methylalumioxane described in the examples and the comparative examples is the ratio of areas in $^{27}$Al-NMR spectrum obtained in accordance with the method described above.

EXAMPLE 1

(1) Preparation of methylaluminoxane

Into 200 ml of toluene, 20.0 g (0.08 mol) of copper sulfate pentahydrate was added. To the obtained solution, 18 g (0.25 mol) of trimethylaluminum was added at −5° C., and the reaction was allowed to proceed at −5° C. for 24 hours to obtain a toluene solution of methylaluminoxane.

$^{27}$Al-NMR spectrum of the obtained methylaluminoxane was measured, and the $A_1/A_2$ ratio was obtained. The ratio was found to be 0.01. The ratio by mol of water taking part in the reaction to trimethylaluminum was 0.8.

(2) Polymerization of styrene

Into a 20 ml vessel which had been dried and purged with nitrogen, 10 ml of styrene and 5 micromol of triisobutylaluminum were placed. Then, the vessel was tightly closed and heated to 70° C. Into a 100 ml vessel which had been dried and purged with nitrogen, the toluene solution of methylaluminoxane obtained above in (1) in an amount of 11.2 mmol expressed in terms of methylaluminoxane, 3.8 mmol of triisobutylaluminum, 150 micromol of pentamethylcyclopentadienyltitanium trimethoxide, and toluene were placed and mixed together to prepare 50 ml of a solution of a preliminarily mixed catalyst.

The solution of the preliminarily mixed catalyst obtained above in an amount of 83 μl was added to the vessel containing styrene and triisobutylaluminum prepared above. The polymerization was allowed to proceed at 70° C. for 1 hour. After the polymerization was finished, the reaction product was dried to obtain 3.11 g of syndiotactic polystyrene (SPS). The catalyst activity was 285 kg/gTi.

EXAMPLE 2

(1) Preparation of methyl aluminoxane

Into 200 ml of toluene, 18 g (0.25 mol) of trimethylaluminum was added, and the obtained solution was cooled to −78° C. To the cooled solution, 3.4 g (0.189 mol) of water from which oxygen had been removed was added dropwise at a rate of 0.01 mol/min during 19 minutes while the temperature of the reaction system was kept at −20° C. The reaction was allowed to continue at 20° C. for further 5 hours to prepare a toluene solution of methylaluminoxane.

$^{27}$Al-NMR spectrum of the obtained methylaluminoxane was measured, and the $A_1/A_2$ ratio was obtained. The ratio was found to be 0.005. The ratio by mol of water to trimethylaluminum was 0.76.

(2) Polymerization of styrene

Styrene was polymerized by using the toluene solution of methylaluminoxane obtained above in (1) in accordance with the same procedures as those conducted in Example 1 (2) to obtain 3.20 g of SPS. The catalyst activity was 294 kg/gTi.

EXAMPLE 3

(1) Preparation of methyl aluminoxane

Into 200 ml of toluene, 18 g (0.25 mol) of trimethylaluminum was added, and the obtained solution was cooled to −50° C. To the cooled solution, 3.4 g (0.189 mol) of water from which oxygen had been removed was added dropwise at a rate of 0.005 mol/min during 38 minutes while the temperature of the reaction system was kept at −30° C. The reaction was allowed to continue at 20° C. for further 5 hours to prepare a toluene solution of methylaluminoxane.

$^{27}$Al-NMR spectrum of the obtained methylaluminoxane was measured, and the $A_1/A_2$ ratio was obtained. The ratio was found to be 0.08. The ratio by mol of water to trimethylaluminum was 0.76.

(2) Polymerization of styrene

Styrene was polymerized by using the toluene solution of methylaluminoxane obtained above in (1) in accordance with the same procedures as those conducted in Example 1 (2) to obtain 2.67 g of SPS. The catalyst activity was 245 kg/gTi.

EXAMPLE 4

(1) Preparation of methylaluminoxane

Into 200 ml of toluene, 23.5 g (0.094 mol) of copper sulfate pentahydrate was added. To the obtained solution, 18 g (0.25 mol) of trimethylaluminum was added at 0° C., and the reaction was allowed to proceed at 0° C. for 24 hours to obtain a toluene solution of methylaluminoxane.

The content of the portion insoluble in a mixed solvent of toluene and hexane in a ratio by volume of 2:5 at 30° C. or lower was measured and found to be 27.7% expressed in terms of aluminum atom.

(2) Polymerization of Styrene

Styrene was polymerized by using the toluene solution of methylaluminoxane obtained above in (1) in accordance with the same procedures as those conducted in Example 1 (2) to obtain 3.16 g of SPS. The catalyst activity was 290 kg/gTi.

EXAMPLE 5

(1) Preparation of methyl aluminoxane

Into 200 ml of toluene, 18 g (0.25 mol) of trimethylaluminum was added, and the obtained solution was cooled to −78° C. To the cooled solution, 3.6 g (0.20 mol) of water from which oxygen had been removed was added dropwise at a rate of 0.005 mol/min during 40 minutes while the temperature of the reaction system was kept at −20° C. The reaction was allowed to continue at 25° C. for further 5 hours to prepare a toluene solution of methylaluminoxane.

The content of the portion insoluble in a mixed solvent of toluene and hexane in a ratio by volume of 2:5 at 30° C. or lower was measured and found to be 14.3% expressed in terms of aluminum atom. The ratio by mol of water to trimethylaluminum was 0.80.

(2) Polymerization of styrene

Styrene was polymerized by using the toluene solution of methylaluminoxane obtained above in (1) in accordance with the same procedures as those conducted in Example 1 (2) to obtain 2.86 g of SPS. The catalyst activity was 260 kg/gTi.

EXAMPLE 6

(1) Preparation of methyl aluminoxane

Into 200 ml of toluene, 18 g (0.25 mol) of trimethylaluminum was added, and the obtained solution was cooled to −50° C. To the cooled solution, 3.6 g (0.20 mol) of water from which oxygen had been removed was added dropwise at a rate of 0.005 mol/min during 40 minutes while the temperature of the reaction system was kept at −10° C. The reaction was allowed to continue at 22° C. for further 5 hours to prepare a toluene solution of methylaluminoxane.

The content of the portion insoluble in a mixed solvent of toluene and hexane in a ratio by volume of 2:5 at 30° C. or lower was measured and found to be 6.7% expressed in terms of aluminum atom. The ratio by mol of water to trimethylaluminum was 0.80.

(2) Polymerization of Styrene

Styrene was polymerized by using the toluene solution of methylaluminoxane obtained above in (1) in accordance with the same procedures as those conducted in Example 1 (2) to obtain 2.40 g of SPS. The catalyst activity was 200 kg/gTi.

EXAMPLE 7 (Polymerization of ethylene)

Into an autoclave which had an inner volume of 1 liter and had been purged with nitrogen, 400 ml of toluene, the aluminoxane used in Example 1 in an amount of 1 mmol expressed in terms of aluminum atom, and 5 micromol of biscyclopentadienylzirconium dichloride were successively added, and the temperature of the resultant mixture was increased to 80° C.

Then, ethylene was continuously introduced into the above autoclave, and the polymerization was allowed to proceed under a pressure of 8 kg/cm² for 1 hour. After the reaction was finished, the catalyst was decomposed by adding methanol, and the obtained product was dried to obtain 131 g of polyethylene. The catalyst activity was 287 kg/gZr.

EXAMPLE 8 (Polymerization of propylene)

The same procedures as those conducted in Example 7 were conducted except that ethylenebisindenylzirconium dimethyl was used in place of biscyclopentadienylzirconium dichloride and propylene was used in place of ethylene, and 92 g of polypropylene was obtained. The catalyst activity was 194 kg/gZr. The isotacticity of the obtained polypropylene was 72% expressed in terms of the pentad fraction (the mmmm fraction).

COMPARATIVE EXAMPLE 1
(1) Preparation of methyl aluminoxane

Into 200 ml of toluene, 18 g (0.25 mol) of trimethylaluminum was added, and the obtained solution was cooled to 5° C. To the cooled solution, 3.6 g (0.20 mol) of water from which oxygen had been removed was added dropwise at a rate of 0.001 mol/min during 4.2 hours while the temperature of the reaction system was kept at −5° C. The reaction was allowed to continue at 22° C. for further 5 hours to prepare a toluene solution of methylaluminoxane.

$^{27}$Al-NMR spectrum of the obtained methylaluminoxane was measured, and the $A_1/A_2$ ratio was obtained. The ratio was found to be 0.2.

The content of the portion insoluble in a mixed solvent of toluene and hexane in a ratio by volume of 2:5 at 30° C. or lower was measured and found to be 4.5% expressed in terms of aluminum atom. The ratio by mol of water to trimethylaluminum was 0.80.

(2) Polymerization of styrene

Styrene was polymerized by using the toluene solution of methylaluminoxane obtained above in (1) in accordance with the same procedures as those conducted in Example 1 (2) to obtain 1.63 g of SPS. The catalyst activity was 150 kg/gTi.

INDUSTRIAL APPLICABILITY

The organic aluminoxy compound of the present invention has the specific characteristics and can provide a homogeneous catalyst having stable and high activity.

The catalyst for producing a polymer of the present invention which comprises the above organic aluminoxy compound as a component has high and stable activity and can provide homopolymers and copolymers of olefins and styrenes with industrial advantages.

We claim:

1. An organic aluminoxy compound, which exhibits a $^{27}$Al nuclear magnetic resonance spectrum ($^{27}$Al-NMR spectrum) having an $A_1/A_2$ ratio of at most 0.1, wherein $A_1$ is an area of a region encompassed by a segment of a line which connects a local minimum point existing between a continuous curve "a" containing a peak appearing at around 150 ppm and a continuous curve "b" containing a peak appearing at around 60 ppm to the point where the above curve "b" comes into contact with the base line and also by the above curve "b", and $A_2$ is an area of a region encompassed by the above curves "a" and "b" and also by the base line, which contains at least 5%, expressed in terms of aluminum atoms, of a portion insoluble in a mixed solvent of toluene and hexane in a ratio by volume of about 2:5 at 30° C. or lower, and being formed from an organoaluminum compound having the formula:

$$R^3Al$$

wherein R represents an alkyl group having 1 to 3 carbon atoms, which are the same or different from each other.

2. The organic aluminoxy compound of claim 1, wherein the organoaluminum compound $R^3Al$ is selected from the group consisting of trimethylaluminum, triethylaluminum, tri-n-propylaluminum, and triisopropylaluminum.

3. The organic aluminoxy compound of claim 1, which is prepared by reacting said organoaluminum compound in an organic solvent with water.

4. The organic aluminoxy compound of claim 3, wherein said reaction is conducted at 0° C. or lower.

5. The organic aluminoxy compound of claim 4, wherein said reaction is conducted at from 0° C. to −100° C.

6. The organic aluminoxy compound of claim 3, wherein said reaction comprises adding water to said organoalumium compound in organic solvent at a rate of about 0.1 mol/min or less per 1 mol of said organoaluminum compound.

7. The organic aluminoxy compound of claim 3, wherein said organic solvent is selected from the group consisting of n-pentane, isopentane, hexane, heptane, octane, nonane, decane, tetradecane, cyclohexane, benzene, toluene, xylene and ethylbenzene.

8. The organic aluminoxy compound of claim 1, which is selected from the group consisting of methylaluminoxane, ethylaluminoxane, n-proplaluminoxane and isopropylaluminoxane.

9. Methylaluminoxane, which exhibits a $^{27}$Al nuclear magnetic resonance spectrum ($^{27}$Al-NMR spectrum) having an $A_1/A_2$ ratio of at most 0.1, wherein $A_1$ is an area of a region encompassed by a segment of a line which connects a local minimum point existing between a continuous curve "a" containing a peak appearing at around 150 ppm and a continuous curve "b" containing a peak appearing at around 60 ppm to the point where the above curve "b" comes into contact with the base line and also by the above curve "b" and $A_2$ is an area of a region encompassed by the above curves "a" and "b" and also by the base line, which contains at least 5%, expressed in terms of aluminum atoms, of a portion insoluble in a mixed solvent of toluene and hexane in a ratio by volume of about 2:5 at 30° C. or lower.

10. A catalyst for producing a polymer, comprising (A) a transition metal compound, and (B) the organic aluminoxy compound of claim 1.

11. A catalyst for producing a polymer, comprising (A) a transition metal compound, (B) the organic aluminoxy compound of claim 1, and (c) a metal compound containing an alkyl group.

12. The catalyst for producing a polymer, comprising (A) a transition metal compound, and (B) the methylaluminoxane of claim 2.

13. A catalyst for producing a polymer, comprising (A) a transition metal compound, (B) the methylaluminoxane of claim 2, and (C) a metal compound containing an alkyl group.

14. The catalyst of any one of claims 10, 11, 12 or 13, wherein said transition metal compound (A) has the formula:

$$MR^1{}_aR^2{}_bR^3{}_cR^4{}_{4-(a+b+c)}$$

or the formula:

$$MR^1{}_aR^2{}_bR^3{}_{3-(d+e)}$$

wherein M is a metal of any one of any one of Groups 3 to 10 of the Periodic table or a metal of the lanthamide group;

$R^1$, $R^2$, $R^3$ and $R^4$ each independently represent alkyl, alkoxy, alkythio, aryl, cyclopentadienyl, substituted cyclopentadienyl, indenyl, substituted indenyl, fluorenyl, amino, amido, acyloxy, phosphide, halogen or a chelating ligand; a, b and c each independently represent an integer of 0 to 4; d and e each independently represent an integer of 0 to 3; or wherein any two of $R^1$, $R^2$, $R^3$ and $R^4$ are bonded to each other via —$CH_2$— or —$Si(CH_3)_2$—.

15. The catalyst of claim 14, wherein the metal M is titanium.

* * * * *